(12) United States Patent
Wu

(10) Patent No.: US 8,258,468 B2
(45) Date of Patent: Sep. 4, 2012

(54) ION MOBILITY SPECTROMETER APPARATUS AND METHODS

(75) Inventor: Ching Wu, Acton, MA (US)

(73) Assignee: Excellims Corporation, Acton, MA (US)

( * ) Notice: Subject to any disclaimer, the term of this patent is extended or adjusted under 35 U.S.C. 154(b) by 153 days.

(21) Appl. No.: 12/723,439

(22) Filed: Mar. 12, 2010

(65) Prior Publication Data

US 2010/0224776 A1    Sep. 9, 2010

Related U.S. Application Data

(63) Continuation of application No. 11/674,646, filed on Feb. 13, 2007, now Pat. No. 7,705,296.

(51) Int. Cl.
*H01J 49/00* (2006.01)
*H04J 49/10* (2006.01)

(52) U.S. Cl. .................. 250/288; 250/286; 250/281

(58) Field of Classification Search .................. 250/286, 250/282, 281, 288
See application file for complete search history.

(56) References Cited

U.S. PATENT DOCUMENTS

| | | | |
|---|---|---|---|
| 7,071,465 B2 * | 7/2006 | Hill et al. | 250/286 |
| 7,414,242 B2 * | 8/2008 | Hill et al. | 250/288 |
| 7,777,180 B2 * | 8/2010 | Hill et al. | 250/286 |
| 2005/0109930 A1 * | 5/2005 | Hill et al. | 250/286 |
| 2006/0186333 A1 * | 8/2006 | Hill et al. | 250/288 |
| 2009/0078861 A1 * | 3/2009 | Hill et al. | 250/282 |

* cited by examiner

*Primary Examiner* — Nikita Wells
*Assistant Examiner* — Johnnie L Smith

(57) ABSTRACT

An ion mobility spectrometer includes a protective housing. A drift tube having at least one inlet and at least one outlet confines a drift gas. An ion gate is positioned in the drift tube. The ion gate defines a reaction region and a drift region in the drift tube. An ion detector is positioned in the drift tube downstream of the ion gate at an end of the drift region. A helical resistive wire coil is positioned around the drift tube. A power supply generates an electric field in the helical resistive wire coil that rapidly controls the temperature of the drift gas.

8 Claims, 7 Drawing Sheets

ION MOBILITY SPECTROMETER APPARATUS AND METHODS

CROSS-REFERENCE TO RELATED APPLICATIONS

This application is a continuation of U.S. patent application Ser. No. 11/674,646, filed Feb. 13, 2007, the entire content of which is herein incorporated by reference.

BACKGROUND OF THE INVENTION

The basic components of a typical ion mobility spectrometer (IMS) include an ionization source, a drift tube that includes a reaction region, an ion shutter grid, a drift region, and an ion detector. In gas phase analysis, the sample to be analyzed is introduced into the reaction region by an inert carrier gas, ionization of the sample is often accomplished by passing the sample through a reaction region and/or an ionization region. The generated ions are directed toward the drift region by an electric field that is applied to drift rings (sometime referred as guard rings or ion guide) that establish the drift region. A narrow pulse of ions is then injected into, and/or allowed to enter, the drift region via an ion shutter grid. Once in the drift region, ions of the sample are separated based upon their ion mobilities. The arrival time of the ions at a detector is an indication of ion mobility, which can be related to ion mass. However, one skilled in the art appreciates that ion mobility is not only related to ion mass, but rather is fundamentally related to the ion-drift gas interaction potential, which is not solely dependent on ion mass.

State-of-the art ion mobility spectrometers include drift tubes with complicated mechanic parts. Each component in the drift tube typically requires the assembly of multiple parts. Such complex mechanical designs significantly increase the cost of ion mobility spectrometer and can also limit the performance of the ion mobility spectrometer. In general, the more parts in the drift tube design, then the higher probability that the drift tube will have technical problems, such as gas leakage, inadequate temperature control, inadequate pressure control, thermal and/or electrical insulation leakage.

For many applications, such as explosive detection in highly contaminated field environments, normal operation of the spectrometer is frequently prevented by overloading the system with large samples or contaminants. Rapid self cleaning mechanisms are highly desired for these applications. Conventional ion mobility spectrometer drift tube constructions are described by Ching Wu, et al., "Construction and Characterization of a High-Flow, High-Resolution Ion Mobility Spectrometer for Detection of Explosives after Personnel Portal Sampling" Talanta, 57, 2002, 123-134. The large thermal mass of the tube structure prevents the system from flash heating and rapid cooling of the ion mobility spectrometric components for cleaning purpose. Spectrometric components can be cleaned by "baking out" the components. However, "baking out" typically takes hours to complete.

Previous publications have indicted that a uniform electric field in the drift region of an ion mobility spectrometer is imperative to achieve high mobility resolution in such devices. See, for example, Ching Wu, et al., "Electrospray Ionization High Resolution Ion Mobility Spectrometry/Mass Spectrometry," Analytical Chemistry, 70, 1998, 4929-4938. A uniform electric field can be created by reducing the size of each voltage drop step and increasing the number of drift rings. Narrow drift rings are utilized to generate the desired field distribution. However, the more drift rings that are used in a drift tube, the more lead wires are needed to be sealed at the wall to complete the drift tube structure. Structure complication greatly limits the possibility of creating highly uniform electric fields in the drift tube. U.S. Pat. No. 4,7120,080 and U.S. Patent Publication No. 2005/0211894 A1 describe layers of conductive coating that are commonly proposed to build the drift tube. However, coatings that are exactly the same thickness along the drift tube are a very challenging to make. Conductive layers with uneven coating thickness will cause distorted electric field distributions and unpredictable system performance.

SUMMARY OF THE INVENTION

The present invention relates to ion mobility spectrometers and to methods of operating ion mobility spectrometers. In one embodiment, the ion mobility spectrometer of the present invention uses a simplified ion mobility spectrometer design having helical resistive material, such as helical resistive wire. The helical resistive wire forms substantially constant electric fields that guide ion movements. The drift tube for ion mobility spectrometers described herein is constructed with a non-conductive frame, resistance wires, an ion gate assembly, a protective tube, flow handling components, and an ion detector assembly. In some embodiments, single or plural resistance wires are wrapped on the non-conductive frame to form coils in various shapes, such as round, oval, square, rectangular, or other polygons shapes. The coil generates an even and continuous electric field that guides ions drift through the ion mobility spectrometer.

In addition to forming the electric field, the helical resistive coil can increase the temperature of the drift tube and any gases flowing through the drift tube. In some embodiments of the ion mobility spectrometer of the present invention, the drift tube temperature is controlled by using the helical resistive coil and a heating element that preheats the drift gas to the designed temperature. The drift gas is delivered directly inside the coil and pumped away from the gas outlet on the protective housing. This configuration provides a robust ion mobility spectrometer that is simple to build with lower thermal mass along the ion and drift gas path, thus allowing rapid temperature modulation, which is required by some applications.

One feature of the present invention is that the drift tube design described herein enables the ion mobility spectrometer to be built with a lower weight, lower power consumption, lower manufacturing cost, and free of sealants that may out gas. In addition, the drift tube can be isolated from ambient environment using vacuum sealing methods that can sustain pressure levels greater than atmospheric pressure.

In addition, the ion mobility spectrometer configuration described herein provides a means to rapidly change pressure inside of the drift tube during the ion mobility measurement. The resistance coil based drift tube configuration allows operating time-of-flight type IMS under high electric field conditions. Measuring ion mobilities of the same ionic species under both high and low field conditions (E/p ratio) provide additional information for ion identification. Unresolved ion mobility peaks under low field conditions may be separated and identified under high field conditions. Methods of sequentially measuring ion mobilities under different E/p ratio according to the present invention allows correlating low field and high field mobilities for comprehensive ion identification.

BRIEF DESCRIPTION OF THE DRAWINGS

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

FIG. 5A depicts a radial cross section of the four-wire coil. FIG. 5B depicts a local axial cross section view of the four-wire coil.

FIG. 6A depicts a local axial cross section of the concentric coils and detector matrix. FIG. 6B depicts a radial cross section of the detector matrix with multiple Faraday plates that is used to detect ions in an ion mobility spectrometer according to the present invention.

DETAILED DESCRIPTION OF VARIOUS EMBODIMENTS

Figure 1:
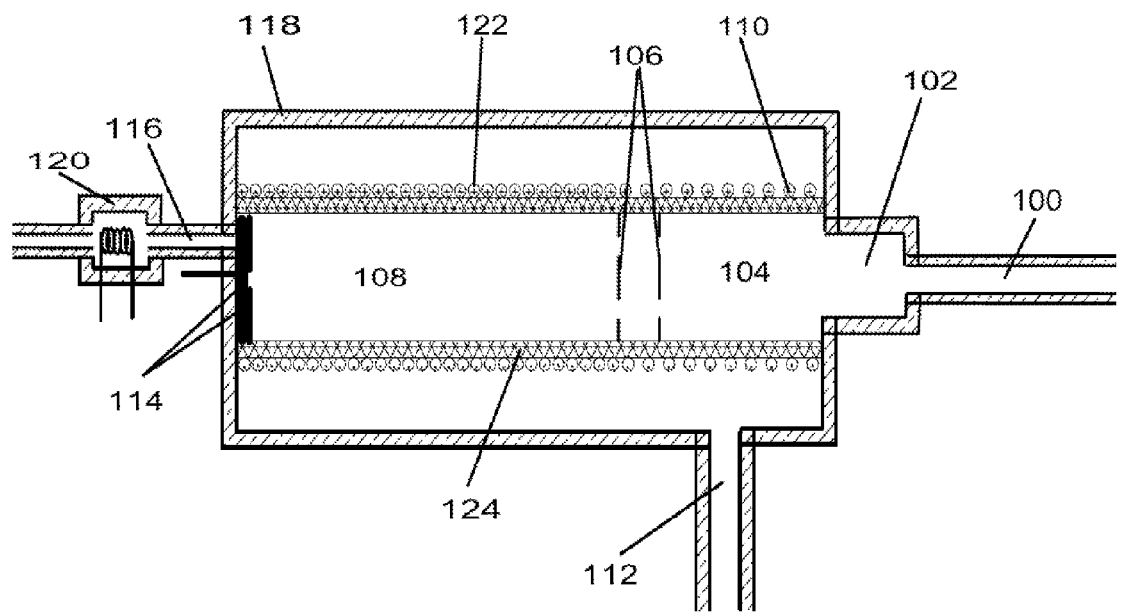
FIG. 1 illustrates a schematic diagram of an embodiment of the ion mobility spectrometer of the present invention.

FIG. 1 illustrates a schematic diagram of an embodiment of the ion mobility spectrometer of the present invention. The sample is introduced to the spectrometer through a sample inlet 100. The sample is ionized while it passes through the ionization source 102. The ionization process is completed in the reaction region 104 before reaching the ion gate assembly 106. In various embodiments, the ion mobility spectrometer described herein can also sample chemicals in ionic form and/or from an external ionization source. The ion gate assembly 106 includes either a Bradbury-Nielsen gate or multiple grids that generate a narrow pulse of ions that is introduce into the drift region 108. Both the reaction region 104 and the drift region 108 of the drift tube are guarded with ion guides.

The ion guides of the present invention are made of a single or a plurality helical coil of resistance wires. The coil of resistance wires used in the reaction region and in drift region can be the same or different coils. In prior art systems, the ion guides (or drift rings) are made of a series of rings with a wire attached to it. The lead wires are brought to the outside of the drift tube and are connected to a series of resistors that divide the drift voltage into multiple voltage drop steps. The ion guide ring and resistor series in prior art systems are replaced by a helical coil that is made of continuous resistance wire 122 wrapped around a supporting frame 124.

As shown in FIG. 1, the reaction 104 and drift region 108 are separated by the ion gate assembly 106. The reaction 104 and drift region 108 can either share the same coil or use different coils. FIG. 1 shows the coil in reaction region 110 has large pitch between wires, which is designed to allow the drift gas to leak into the outer chamber, where it is pumped away from the gas outlet 112. Using wires with different resistivity in these two regions can control the time the ions stay in a giving region. For example, in the reaction region 104, the resistivity of coil can be lower than the resistivity of the coil in the drift region 108. In this example, the ions move at a relatively slow rate in the reaction region 104, which allows the ions to have sufficient time for the ionization reaction to be completed. In some embodiments, the wire resistivities in both the reaction 104 and the drift region 108 are optimized to generate the desired electric field strength.

In other embodiments, the resistivities of the coils for drift 108 and reaction 104 regions can also be adjusted to heat these two regions to different temperatures, respectively. For example, when the drift tube is interfaced to an electrospray ionization source, the reaction needs to be at a relatively higher temperature to assist in the desolvation process. In these embodiments, the resistance of the coil in the reaction region 104 is made to be relatively high. However, if both a lower voltage drop and a higher temperature are desirable in the region, then plural coils may be used in the reaction region 104. The above example shows an alternative embodiment where the drift 108 and reaction 104 region could be build with different coil configurations.

Figure 2:
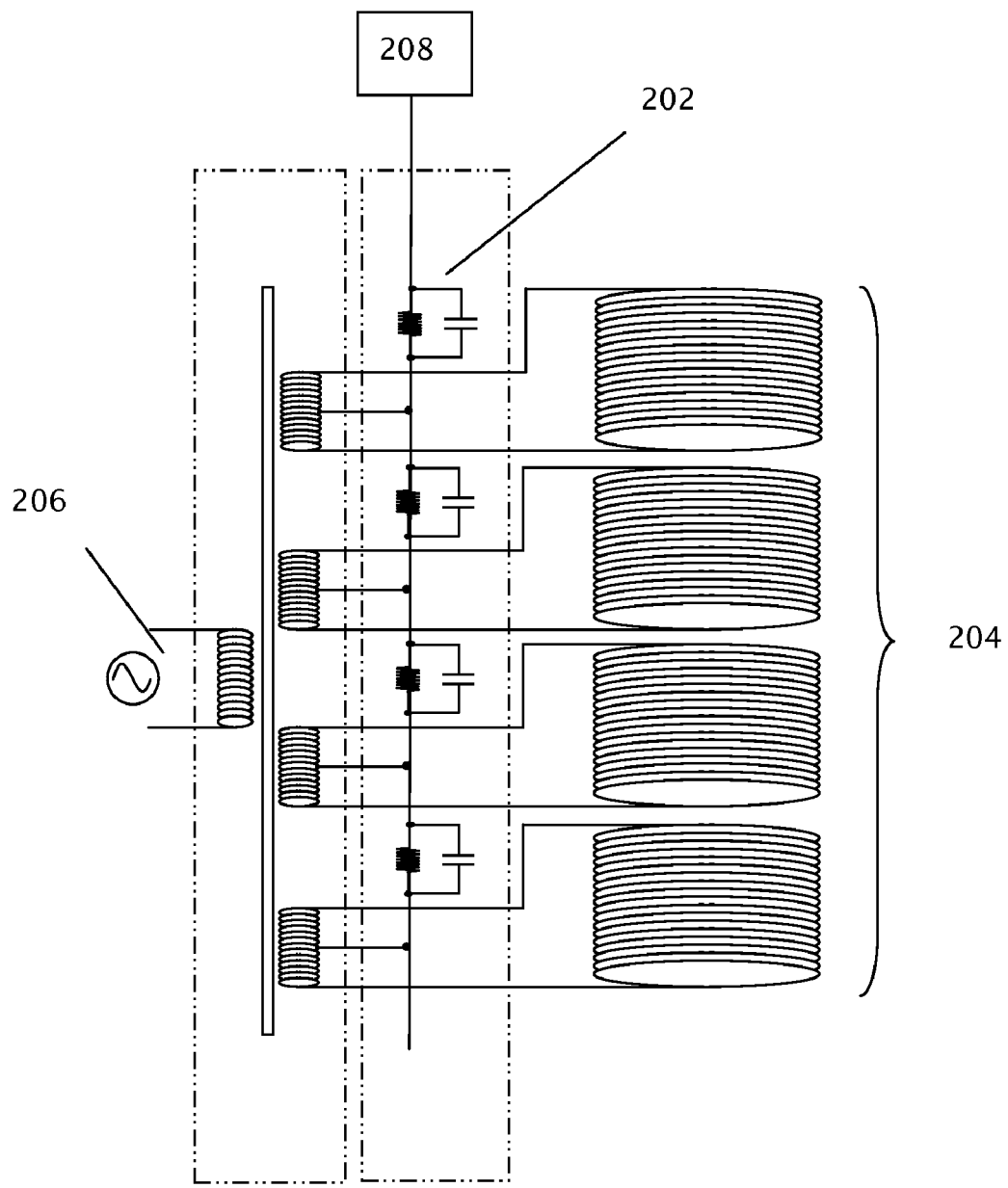
FIG. 2 illustrates an alternative embodiment of the drift tube of the present invention.

FIG. 2 illustrates an alternative embodiment of the drift tube of the present invention. The alternative embodiment shows a segmented resistance coil that is used as an ion mobility drift tube. The sections of the coil are arranged in a similar fashion as the prior art drift rings.

Figure 3:
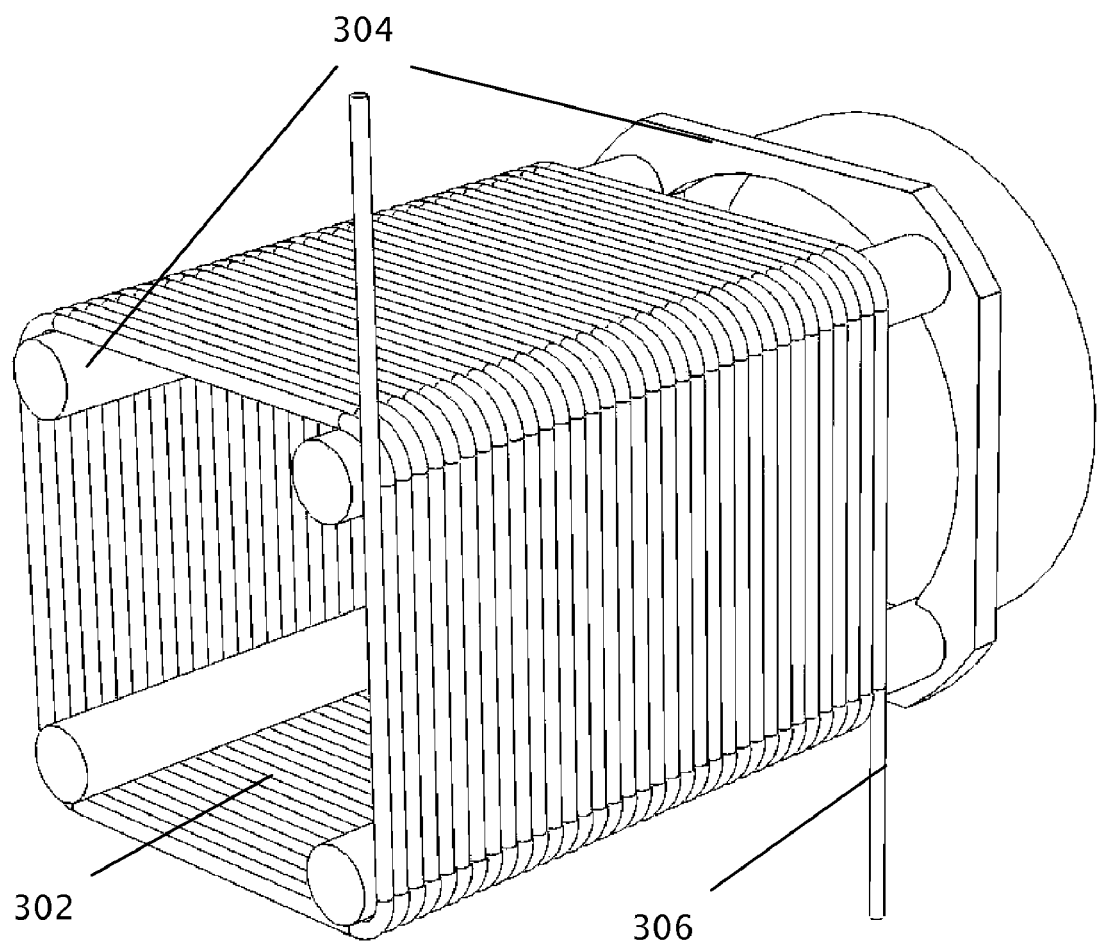
FIG. 3 illustrates a rectangular resistance coil built from a single resistance wire with four-rod supporting frame.

FIG. 3 illustrates a three dimensional drawing of a rectangular resistance coil 302 built from a single resistance wire 306 supported by a four-rod frame 304. The size of the rod can be minimized to avoid charge build up that may influence the electric field distribution inside the drift tube.

In some embodiments, the drift tube is made from multiple coils that are wrapped in opposite directions. Such coils can be formed by using another resistance wire that starts on the same rod as the existing wire, but that is wound in a counter clockwise direction. The wire will meet the other wire on the bottom-left rod. As both of the coils continue, they will overlap at every half turn. In these embodiments, the magnetic field generated from the coil will be effectively cancelled. The ion cyclotron motion under atmospheric pressure is negligible for ion separation. However, under low pressure conditions, the effects from the magnetic field in a resistance coil based ion mobility spectrometer can be significant. In another embodiment, symmetric multiple reverse coils that overlap after a certain number of turns are used to generate a more uniform electric field and can eliminate the effect of the magnetic field in the drift tube.

Figure 4:
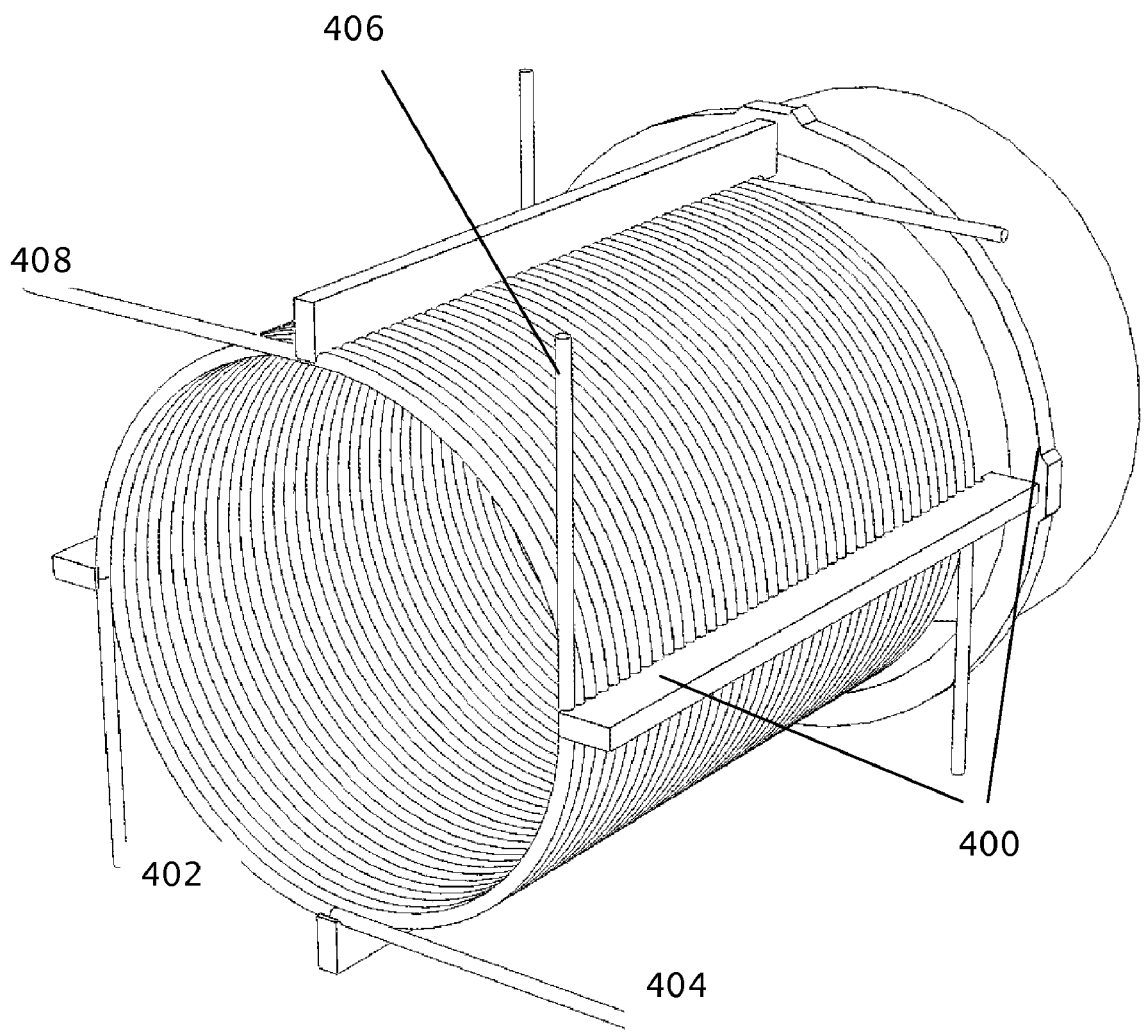
FIG. 4 illustrates a round resistance coil built from four resistance wires on a supporting frame.

Depending on the drift tube design, the ion guide of the present invention can also be formed of a plurality of coils. FIG. 4 illustrates a round drift tube comprising four resistance coils on a supporting frame 400. The four coils 402, 404, 406, and 408 started at the same level in the axis direction, but are offset by 90 degrees. Different numbers of resistance coils can be used depending on the desired electric field uniformity requirements. In some embodiments, the electric field uniformity is improved by increasing the number of coils. However, in these embodiments, material with higher resistivities is used in order to maintain the same level of power consumption. The resistance coil can be formed in many different shapes depending on the frame design, such as round, rectangular, oval, or other polygons. One skilled in the art will appreciate that the resistance coil can be formed in an almost unlimited number of shapes.

Figure 5A:
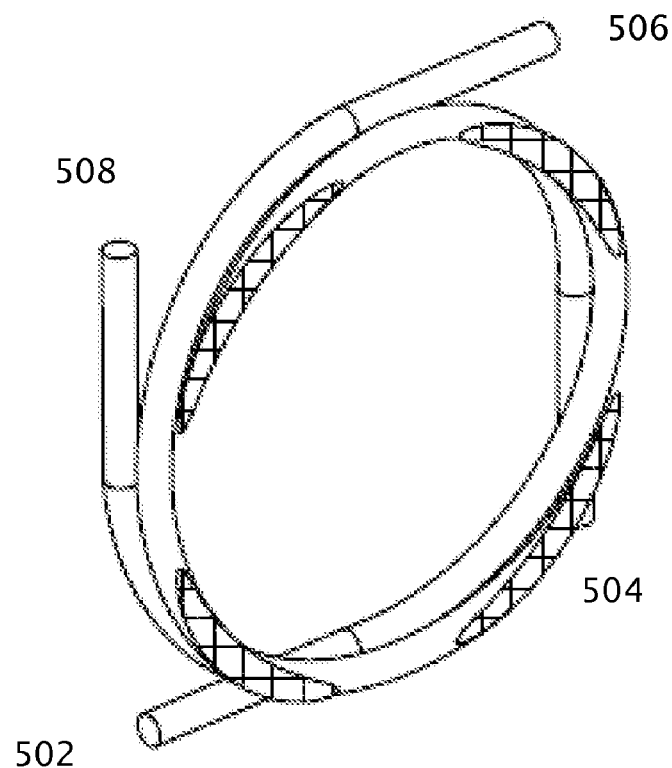
FIGS. 5A and 5B illustrate cross-sectional views of the four-wire coil.
Figure 5B:
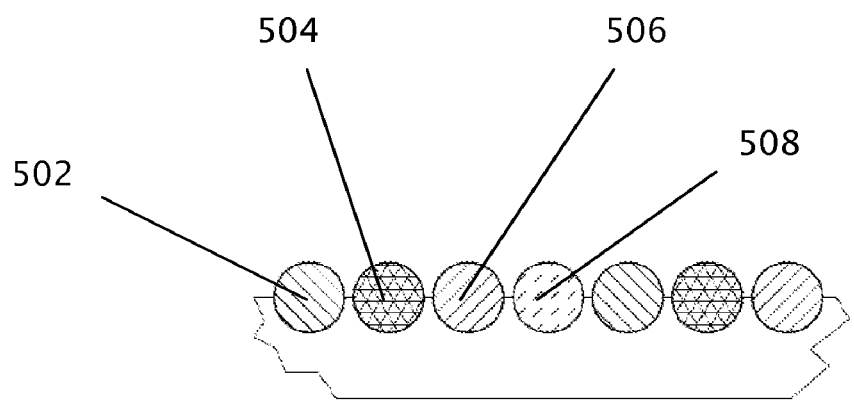

FIG. 5A illustrates the radial cross sectional view of the four coil drift tube. In many embodiments, the same voltage is applied to all four wires 502, 504, 506, and 508. The cross section view shows ions in the center of the drift tube experience a symmetric electric field that causes the ions to drift along the axis similar to the conventional ion mobility spectrometer drift tubes. FIG. 5B illustrates an axial cross sectional view of the four coils. The four wires 502, 504, 506, and 508 are separated with a distance that is chosen to prevent arcing between the wires. The distance is also optimized to shield the drift region from outside electric fields.

After ions are introduced into the drift region 108, the ions travel toward the ion detection assembly 114 under the influence of an electric field. The ions are then detected as an ion current on the detector matrix. During the time that the ions travel in the drift region 108, they are separated based on their ion mobility. The ion gate assembly 106 normally consists of a set of parallel wires where adjacent wires in the set of parallel wires can be set to different voltages (Bradbury-Nielsen gate). The ion gate assembly 106 may also be made of two parallel grids that perform a push-pull type of ion extraction. An example of push-pull type ion extraction is setting the downstream grid at a relatively low voltage and the upstream grid at a relative high voltage briefly during ion extraction. Ions between the two grids are then ejected into drift region 108 in a pulse form. In some embodiments, the downstream grid is replaced by a Bradbury-Nielsen gate. The Bradbury-Nielsen gate can be opened for a shorter time duration than the time duration that a higher voltage is applied on the upstream grid. In these embodiments, a combination of Bradbury-Nielsen gate and push-pull type ion extraction generates a narrow pulse with a high ion density. The gate is used to control the ion pulse width.

The detector assembly consists of an aperture grid and a detector matrix. FIG. 6B illustrates a detector matrix with multiple Faraday plates that is used to detect ions in an ion mobility spectrometer according to the present invention. The detector matrix illustrated in FIG. 6B is a segmented single Faraday plate. In the embodiment shown, the single Faraday plate is segmented into multiple Faraday plates in a circular design. The number of the segments depends on the desired detector resolution.

Multiple coil ion mobility spectrometers use the detector matrix to detect spatially resolved ions in the radial direction under the influence of the radial direction electric field. The detector matrix can also be used with an ordinary ion mobility spectrometer, which is similar to Configuration A 702 described in connection with FIG. 7, to selectively read out ion current at different radial locations. The selective reading method can improve ion mobility spectrometer resolution by eliminating the effect of diffusion in the radial direction and non-uniform electric field distribution close to drift tube wall.

For example, a resistance coil drift tube can be built using resistance wire of Iron Chrome Aluminum Molybdenum alloy that has electrical resistivity of 153 Microhms/cm-.sup.3. When selecting a wire in "ribbon" form, with 0.035 mm in thickness and 0.08 mm in width, the wire has resistance of 603 ohms/m. To build a drift tube of 2.54 cm i.d. and 4 cm total length, 32 meters of the resistance wire is needed (assuming the drift electric field strength is 200 V/cm and the total power consumption is 33 W). Similarly, with the same material in round shape, 0.05 mm in diameter, the resistance is 728 ohm/m. Assuming a 4 cm total drift length, 42.5 meters of resistance wire is used. The same drift field of 200 V/cm is achieved and the total power consumption is 20 W.

As described herein, in one embodiment of the invention, a single resistance wire may also function as a 33 or 20 W heater for the spectrometer. Such a heater will eliminate the heating element required in prior art conventional ion mobility spectrometers. In these embodiments, the resistance coil functions as an electric field barrier to guard the drift 108 and reaction 104 region, and also as a temperature barrier that guarantees drift and reaction region temperature.

Referring to FIG. 1, the drift flow is introduced to the spectrometer at the drift gas inlet 116 that is located behind the detector assembly 114. The drift gas enters the drift region 108 (inside of the resistance coil) after being preheated. The resistance coil maintains the drift gas temperature after it enters the drift tube. As the drift gas flows toward the ionization source 102, it also leaks out through the coil into the outer space between the resistance coil and the spectrometer housing 118. If the resistance coil has a large pitch in the reaction region 104 as shown in FIG. 1, the majority of the drift gas exits from the reaction region 104 section of the drift tube and is pumped away via the gas outlet 112. Excessive sample and sample carrier gas are also pumped away from the same outlet. Note that in an alternative embodiment, the sample inlet 100 can also be used as gas outlet if the gas outlet 112 is used as sample inlet. In order to use the gas outlet 112 as the sample inlet, a nonconductive tube needs to be used to deliver samples to the inside of the resistance coil.

The drift tube of the present invention can be rapidly heated or cooled down because of the low thermal mass construction. The drift tube temperature is controlled by the drift gas pre-heater 120 and the resistance coil. The drift tube of the present invention eliminates all ceramic or glass tubing and other heavy and/or complex components. The pre-heater 120 shown in FIG. 1 directly exposes high temperature heating wire to the drift gas. If the drift gas is recycled using a closed loop wherein the inlet and outlet for the drift gas are connected to form a circulatory gas system, the high temperature zone in the pre-heater 120 may also be used to cause thermal decomposition of contaminants in the drift gas. Catalytic material may also be used in the pre-heater 120 for gas regeneration.

This invention eliminates the majority of the lead wires of the drift rings used in prior art conventional ion mobility designs. The electrical contacts that need to feed through the protective housing 118 are one high voltage power supply wire, a signal cable for the detector matrix, and lead wires for ion gate assembly 106. The ion mobility spectrometer of the present invention has relatively few feed-through devices. The protective housing 118 can completely seal the drift tube from the ambient conditions. By regulating the flow of drift gas and sample inlet/outlet, the ion mobility spectrometer can operate under controlled pressure conditions.

In one embodiment, the resistance coil is segmented into multiple sections that are arranged sequentially to form a continuous constant electric field in the reaction region or in the drift region. The multiple resistance coils could be used to achieve the same performance for rapid spectrometer heating and cooling, and other IMS operating conditions. The segmented coils do not require using high resistance wires to form the coil as they could be interconnected using the voltage divider circuit shown in FIG. 2. There is only a small voltage drop across the segmented coils. The resistivity of the coil is only required to heat the drift tube. A voltage divider circuit 202 is used to define the drift field for ions traveling in the drift tube. FIG. 2 shows a portion of the drift tube that is made of segmented resistance coils 204, where an AC power supply 206 is used to drive the coils. A high voltage DC power supply 208 is used to define the drift field through a high voltage divider circuits.

The ion mobility spectrometer of the present invention can operate under a continuous pressure gradient which achieves separation in both high (>2 V/cm-torr) and low (<2 V/cm-torr) field conditions. In low field conditions, the ion mobility is a constant for a given ionic species. However, the ion mobility is no longer constant under high field conditions. The mobility change vs. field condition characteristics (E/p, where E is the electric field strength and p is the pressure) is dependent on the particular ionic species being in the drift tube. Operating an ion mobility spectrometer in high field conditions can separate ions that are inseparable in low field conditions.

The field condition is related to the drift field strength and to the operating pressure. Scanning through a wide range of drift voltage is difficult. In one embodiment, the ion mobility spectrometer of the present invention forms a continuous pressure gradient that generates low/high field conditions which achieve maximum separation based on both constant and differential mobility of ions.

Drift field strengths in prior art ion mobility spectrometers are in the range of 200 V/cm to 500 V/cm depending on the size of the molecules being separated. Using a drift field strength of 200 V/cm and pressure changes from 760 torr to 1 ton, the E/p ratio changes from a low field condition of 0.26 V/cm-torr to a very high field condition of 760 V/cm-torr. To realize this operating condition, the pressure in the drift tube needs to be pumped from ambient pressure to 1 ton, which can be achieved using commonly available vacuum pumps.

It should be understood that the methods of operation described herein can be applied to any ion mobility spectrometer having the ability to regulate the pressure to create low field and high field conditions. The present invention is not limited to the ion mobility spectrometer described in this invention having the resistance coil configurations.

In operation, samples are introduced into the spectrometer either by sample carrier gas flow or by direct electrospray of liquid samples in the ionization/reaction region. The sample concentration normally lasts from a few seconds to a few minutes. During this period of time when samples are continuously introduced into the instrument, the ion mobility spectrometer acquires significant number of spectra the sample. The pressure gradient may start synchronously or asynchronously with the ion mobility spectra acquisition. Alternatively, the drift tube may be set to one or multiple pressure values that allow measuring ion mobility in different field conditions.

The sample introduction at the sample inlet 100 of the spectrometer may be used as a trigger to start the data acquisition if a mechanical vacuum pump is connected to the gas outlet 112 as shown in FIG. 1 and both the drift gas and the sample inlet flow are restricted to control the pressure in the drift tube. After a few moments of delay or after the target ions have been detected, the vacuum pump starts to reduce the pressure in the drift tube.

The mobility spectra can be plotted in a 3-D figure with ion mobility ($K_o$) as x-axis, ion intensity as y-axis, and the number of spectra as z-axis. Traceable changes of a given ion mobility peak that are a constant under low field conditions will be seen. The peak may start to shift as the time elapses (number or spectra in z-axis increase) and the drift tube entering vacuum conditions. The curve that describes this shifting function (projected on the x-z plane) can be used for chemical identification. The drift tube is typically designed to avoid the generation of arcs between the resistance coil and the surrounding electrodes under the desired vacuum conditions. The distance between high voltage electrodes and the protective housing 118 (which is typically at ground potential) is chosen to reduce the probability of generating an electrical discharge.

Figure 6A:
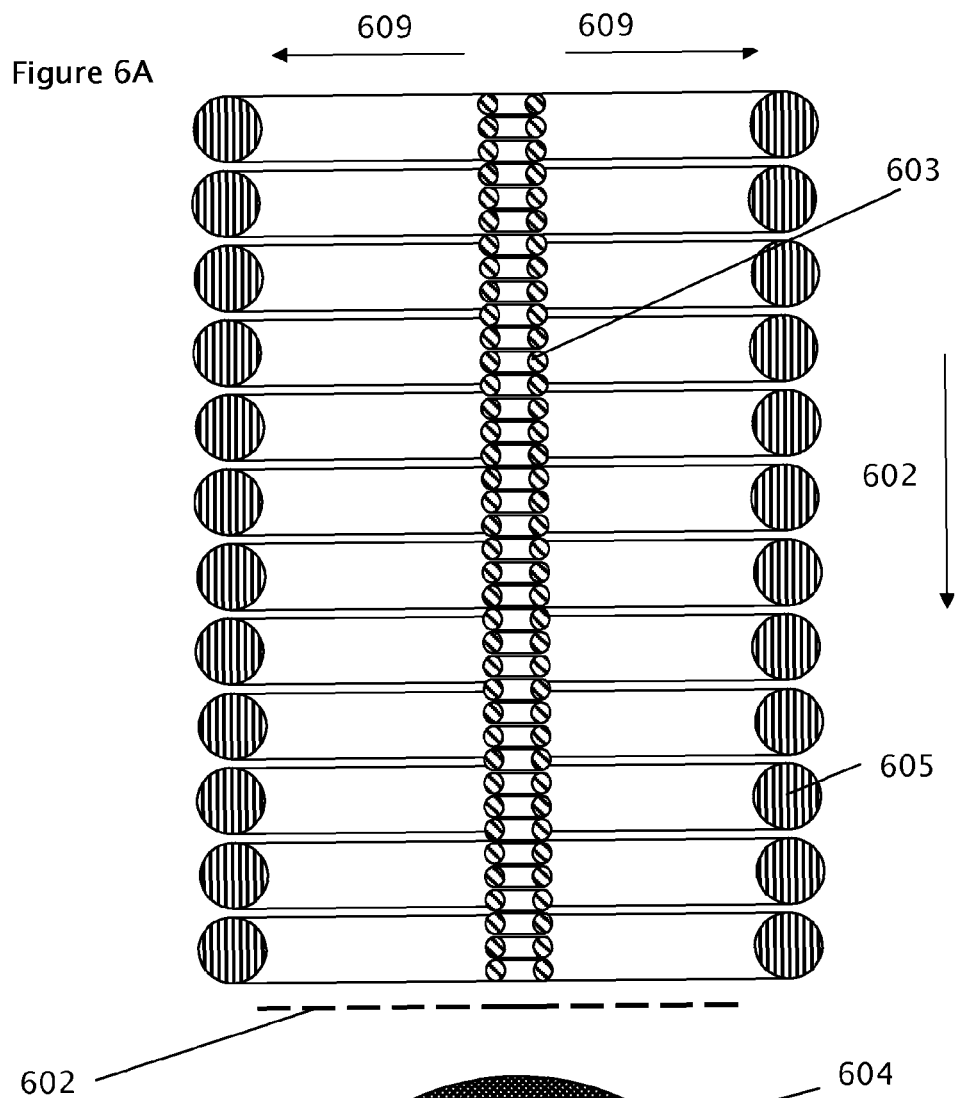
FIGS. 6A and 6B illustrate cross-sectional views of an inner and outer concentric coils and detector matrix.
Figure 6B:
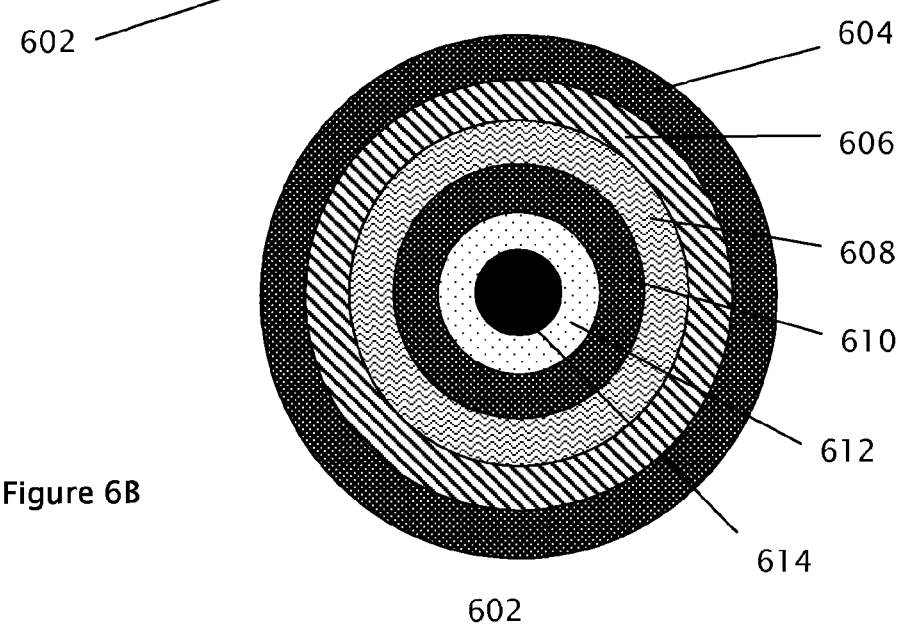

In one embodiment, a multiple resistance coil configuration of ion mobility spectrometer is arranged using concentric coils as shown in FIG. 6A. Given an inner coil 603 having a constant voltage difference in the radial direction from the outer coil 605 along the axis of the coils, ions traveling between the coils experience a force from the electric field in both the radial and the axial direction. Ions can be separated in both the radial and the axial directions simultaneously, thus achieving two dimensional separation. The electric field strength in the axial and the radial directions can be selected to achieve simultaneous high field 607 and low field 609 ion mobility measurements.

Figure 7:
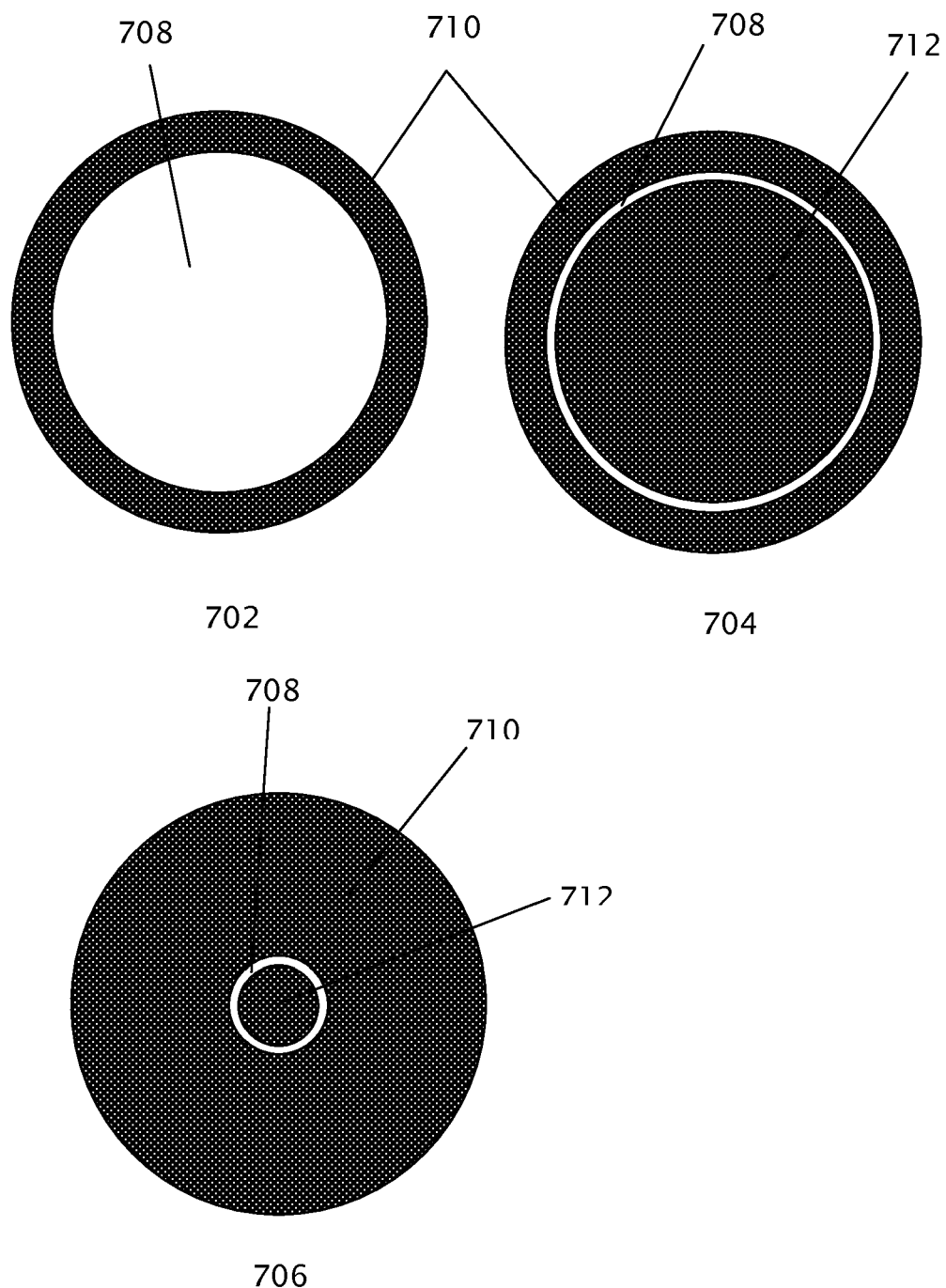
FIG. 7 shows ion source outlet configurations of the ion mobility spectrometer according to the present invention.

FIG. 7 shows ion source outlet configurations of the ion mobility spectrometer according to the present invention. Configuration A 702 introduces uniform ion population along the radial direction. The radial electric fields are used to focus or de-focus the ion beam as they travel through the drift tube. In Configuration B 704, ions are pulsed into the drift tube in a ring shape; with the radial electric force pointing toward the center of the coil. The ions are separated while they are drifting down the drift tube as well as moving toward the center of the drift tube.

Referring back to FIG. 6B, the detector matrix 602 detects the ion current, and also detects the relative location toward the center of the drift tube. Even though the figure only shows six elements 604, 606, 608, 610, 612, and 614 in the detector matrix 602, the matrix may contain any desired number of rings so as to achieve the required radial mobility resolution. The ion motion under the influence of high and low electrical field conditions (E/p) is related to the ion drift conditions in the drift tube, which includes electrical field strength, drift gas properties, pressure, and temperature.

Configuration C 706 shows another embodiment that achieves the two dimensional separation. In this case, the ions are introduced near the center of the drift tube. A de-focusing force is created with an electric field in radial direction. Both ion intensity and location may be detected on the detector matrix. The size and radial location of the ion outlet apertures 708 of the ionization source can be changed by adjusting the outer ring 710 and inner disc 712. The size is adjusted to balance the tradeoff between the resolution and the sensitivity for 2D separation, i.e. reduce aperture size for higher resolution, and increase aperture size for higher sensitivity.

A pulse of ions from the ionization source can either be generated using conventional Bradbury-Nielsen ion gate configuration down stream from the ion outlet aperture 708; or by using inner disc 712 and outer ring 710 as shown in FIG. 7. The gate is closed by applying a voltage across the outer ring 710 and the inner disc 712 and opened by setting 710 and 712 at the same voltage. In this case, the gate assembly can generate ion pulses in the shape of a ring.

What is claimed is:

1. An ion mobility spectrometer comprising:
    a) a inlet through which some ions are introduced into a drift region;
    b) a first electric field that guides ions traveling toward a first direction;
    c) a second electric field that simultaneously guides these ions traveling toward a second direction; and
    d) a detector matrix that detects the ions.

2. The ion mobility spectrometer of claim 1, wherein the first direction is an axial direction.

3. The ion mobility spectrometer of claim 1, wherein the second direction is a radial direction.

4. The ion mobility spectrometer of claim 1, wherein the first and second electric fields are different field conditions (E/p).

5. The ion mobility spectrometer of claim 1, wherein the first electric field is in a high field conditions.

6. A method for operating an ion mobility spectrometer, the method comprising:
    a) introducing ions in a drift region through a inlet;

b) guiding ions with a first electric field traveling toward a first direction;

c) simultaneously guiding ions with a second electric field traveling toward a second direction; and d) detecting ions at a detector matrix.

7. The method of claim 6, wherein guiding ions involves separating them in both a first and second direction.

8. The method of claim 6, wherein detecting ions with both intensity and location.

\* \* \* \* \*